(12) United States Patent
Mannhardt

(10) Patent No.: US 6,266,139 B1
(45) Date of Patent: Jul. 24, 2001

(54) CAPILLARY TUBE HOLDER

(76) Inventor: Joachim Mannhardt, Heergasse 3, D-73569 Eschach (DE)

( * ) Notice: Subject to any disclaimer, the term of this patent is extended or adjusted under 35 U.S.C. 154(b) by 0 days.

(21) Appl. No.: 09/171,766

(22) PCT Filed: Apr. 19, 1997

(86) PCT No.: PCT/EP97/01984

§ 371 Date: Oct. 22, 1998

§ 102(e) Date: Oct. 22, 1998

(87) PCT Pub. No.: WO97/40363

PCT Pub. Date: Oct. 30, 1997

(30) Foreign Application Priority Data

Apr. 23, 1996 (DE) .......................................... 296 07 239 U

(51) Int. Cl.⁷ ...................................................... F01N 1/10
(52) U.S. Cl. .......................................... 356/246; 356/244
(58) Field of Search ...................................... 356/246, 244

(56) References Cited

U.S. PATENT DOCUMENTS 5,408,313  4/1995  Ponstingl et al. .................... 356/246
5,413,686  5/1995  Klein et al. .......................... 204/299

FOREIGN PATENT DOCUMENTS 4024420  2/1992  (DE) .
2643147  8/1990  (FR) .

*Primary Examiner*—Frank G. Font
*Assistant Examiner*—Reginald A. Ratiff
(74) *Attorney, Agent, or Firm*—Lockwood, Alex, Fitzgibbon & Cummings

(57) ABSTRACT

The invention relates to a capillary tube holder with a recess for holding a capillary tube. At least one pair of light channels is provided perpendicular to the axial direction of the recess. Each pair of light channels has an incoming light channel to supply light beams to the capillary tube and an outgoing light channel to transmit said light beams to an evaluation device. The light channels extend radially with respect to the recess and lead therein. Light conductors comprising individual fibres are provided in each incoming light channel and each outgoing light channel and are arranged upstream of the capillary tube. The diameter of each individual fibre corresponds at least approximately to the internal diameter of the capillary tube, and a plurality of individual fibres of the light conductors is arranged parallel and/or radially to the longitudinal axis of the capillary tube in the area where the light channels lead into the recess.

12 Claims, 2 Drawing Sheets

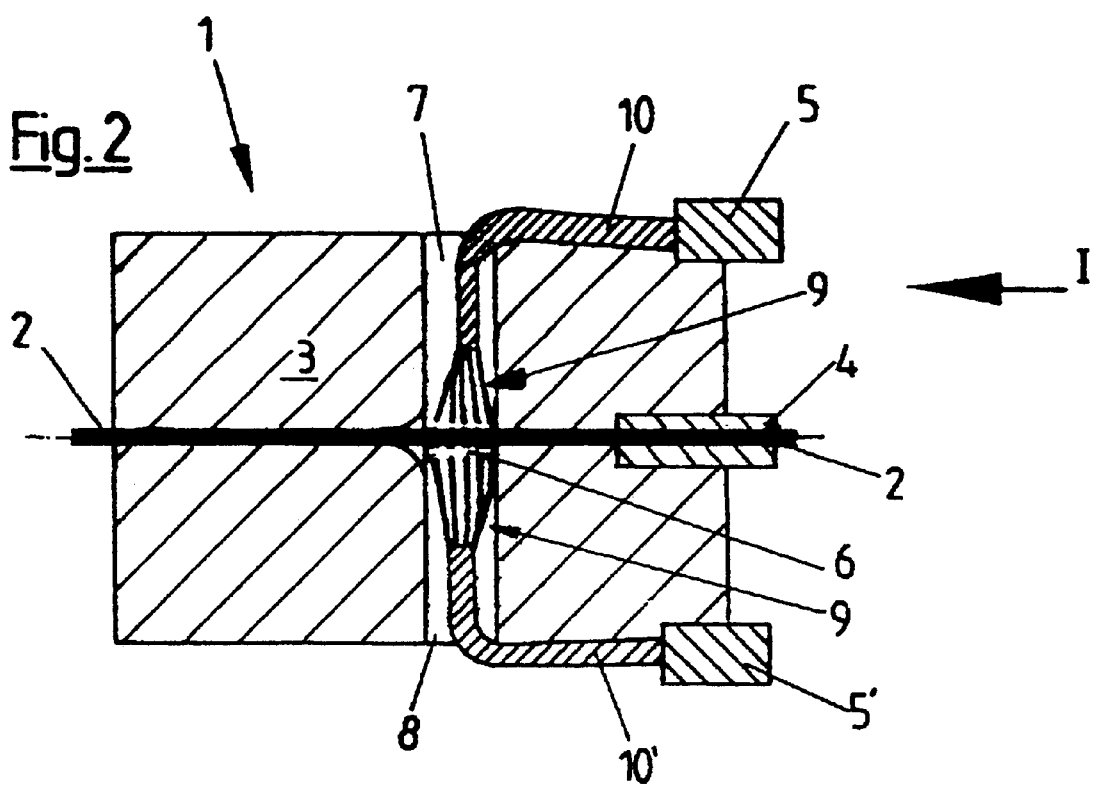
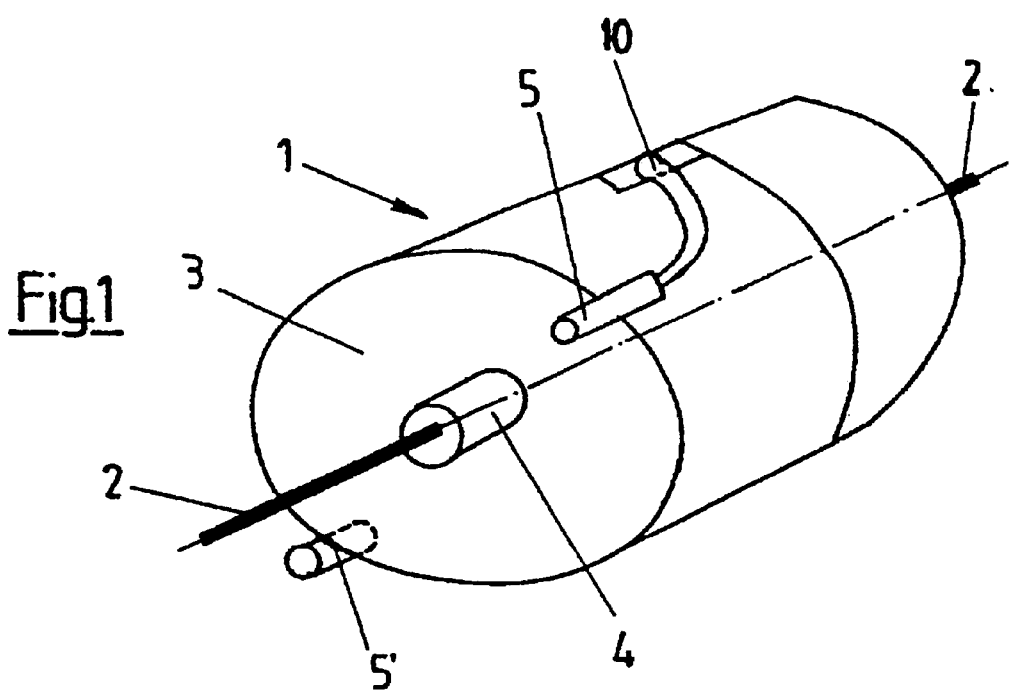

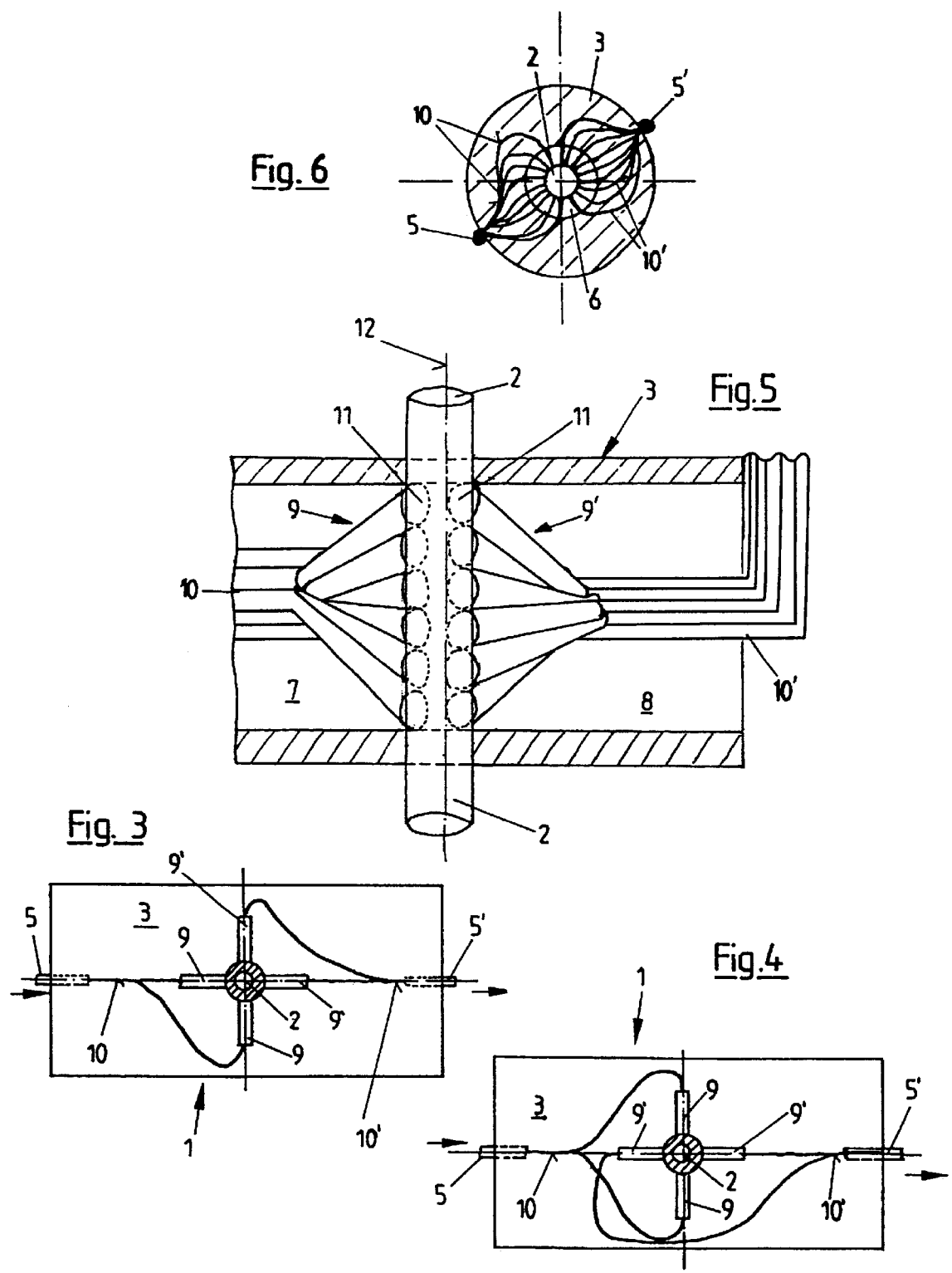

CAPILLARY TUBE HOLDER

The invention relates to a capillary tube holder according to the type defined in more detail in the preamble of claim 1.

Capillary tube holders of the generic type which are used, for example, for microHPLC (micro high performance liquid chromatography) and for CE/CZE (capillary electrophoresis/capillary zone electrophoresis) are known from practice.

In this case, a capillary tube, which usually consists of silica, has a transparent window burned free on it after which the window is cleaned, whereupon the capillary tube is pushed into a recess in the capillary tube holder and adjusted in the capillary tube holder such that the transparent window comes to be situated in the region of two light channels arranged situated opposite one another axially with respect to the capillary tube in the capillary tube holder, it being possible to determine the exact position of the capillary tube and/or the window described in the capillary tube holder by means of the evaluation device such as, for example, a spectrometer.

During the measuring operation with the known capillary tube holders, light beams are led through the input light channel to the transparent window in the capillary tube, there flowing through said capillary tube a medium, in particular a liquid, on which measurements or determinations are to be undertaken.

A suitable optical system for focusing the light beams is provided in the input light channel, the focused light beams passing through the capillary tube or the window in the capillary tube and the medium flowing through the capillary tube, whereupon the light beams are fed through the light output channel to a detector or a spectrometer or another suitable evaluation device.

FR 2 643 147 A1 describes a measuring system having optical components which effect an expansion of light in all directions. An optically imaging element provides transillumination, it being possible to detect only relatively large units. Capillary tube measurements are not possible thereby.

It is also disadvantageous in known capillary tube holders that overall only an insufficient quantity of the light fed through the input light channel passes through the capillary tube, with the result that it is also possible to feed only an insufficient quantity of light to the evaluation device. The reason for this is that the capillary tube has, for example, an inside diameter of only 75 $\mu$m, that is to say the useful quantity of light which can be led through the capillary tube can be distributed only over this cross-sectional surface.

Furthermore, a relatively large proportion of the light fed through the input light channel is led in an unused fashion over the outer wall of the capillary tube to the output light channel, that is to say the light fed does not pass through the medium flowing through the capillary tube, and on the one hand this entails impairment of the measurement result in the evaluation device, and on the other hand it causes a reduction in the sensitivity of the evaluation device, for example a detector or a spectrometer, connected downstream of the capillary tube holder, since the useful component of the light received by the evaluation device, or of the light contributing to the absorption, is too small. Thus, to a substantial extent, the light is not used for absorption of the flow of medium in the capillary tube, but passes through the side wall of the capillary tube in a partially unused fashion.

Since, as already mentioned, this fact has a disadvantageous effect on the sensitivity of the measuring arrangement, the disadvantages described lead to a substantial impairment of the measurement results.

It is therefore the object of the present invention to provide a capillary tube holder which eliminates the described disadvantages of the prior art, in particular in the case of which a larger proportion of the light fed through the input light channel passes through the medium flowing through the capillary tube.

This object is achieved according to the invention by the features mentioned in the characterizing part of claim 1.

As a result of the use of optical conductors with individual fibers, a larger proportion of the light fed to the capillary tube holder is supplied overall to the capillary tube, and thus also to the medium flowing through the capillary tube.

The optical conductors, with the individual fibers, which are used are positioned in this case directly in front of the capillary tube, so that the capillary tube acts as an optical system and deflects the light beam or the light beams, which is/are fed through the input light channel, to such an extent that approximately 90% of the light beams are led through the medium and to the output light channel, that is to say 90% of the light beams participate in the absorption. There is no need in this case for optical imaging, the capillary tube itself, instead, being used for this purpose. Thus, by contrast with the prior art the useful component of the light fed is substantially higher for the capillary tube holder according to the invention.

A slight gap, which is caused, for example, by manufacturing tolerances of the capillary tube, always remains between the respective optical conductor and the capillary tube. Otherwise, the optical conductors are, however, brought as tightly as possible up to the capillary tube.

Since, as fiber bundles, the individual fibers furthermore have in each case a diameter which is at least approximately as large as the inside diameter of the capillary tube, just so much light is fed through each individual fiber that said light is not largely led through the wall of the capillary tube and that, on the other hand, too much light is not unnecessarily fed to the capillary tube.

According to the invention, on the capillary tubes [sic] the incoming light bundle composed of a plurality of individual fibers is either split up in the longitudinal direction or laid around radially in a semicircle, it also being possible to combine the two, that is to say longitudinal and radial directions. In the same way, the outgoing, that is to say the output beams and the receiving optical conductors are arranged in a corresponding way to this.

In a development of the invention, it is possible to provide in this regard that at their ends facing the recess, the optical conductors in each case have a cross section-transforming element for transforming the cross-sectional surface of the optical conductors, that is to say the cross section-transforming elements are a component of the optical conductors.

These cross section-transforming elements can be used to transform the, for example, round cross sections of the optical fibers or of the fiber bundles in the input light channel and the output light channel into other suitable cross sections or cross-sectional shapes, which are described at another juncture.

Cross section-transforming elements of extremely varied design are already known from practice for other applications. The aim is to use the cross section-transforming elements, which are packed as tightly as possible, to achieve the highest possible light power on very small surfaces, and this can be achieved, for example, by virtue of the fact that in the region where the light channels open into the recess a plurality of individual fibers of the optical conductors are arranged parallel to the longitudinal axis of the recess, and therefore along a straight line, that is to say the totality of the individual fibers, which normally has a round cross-sectional surface, is dismantled or transformed into a multiplicity of smaller individual cross sections.

In the arrangement of the optical conductors described, the useful cross-sectional surface of the optical conductors can be optimally adapted to the cross-sectional surface of the capillary tube in a straight line for which a plurality of individual optical fibers with a correspondingly smaller cross-sectional surface lead light beams through the capillary tube.

However, it is also possible as an alternative for a plurality of individual fibers of the optical conductors to be arranged distributed radially over the outside diameter of the recess or of the capillary tube, as a result of which it is likewise possible to achieve the advantages mentioned.

This advantageous arrangement is also not possible until use is made of the cross section-transforming elements already mentioned by means of which a virtually optimum yield of the light fed through the input light channel is possible, that is to say the useful component of the light fed, which is relayed to the evaluation device for evaluation purposes, is particularly high for these two arrangements or embodiments described.

In a development of the invention, it can also be provided that with respect to the recess each output light channel is situated diametrically opposite its assigned input light channel, that is to say the output light channel is located in the extension of the input light channel on the opposite side of the capillary tube or the recess.

This arrangement can be used to measure the absorption of the medium flowing through the capillary tube, since the light or the light beams are led directly through the capillary tube or the flowing medium to the optical conductor in the output light channel.

Alternatively, however, it can also be provided that in the case of two pairs of light channels the two input light channels and the two output light channels are arranged in each case situated diametrically opposite one another with respect to the recess, that is to say an input light channel is situated opposite each input light channel, and likewise an output light channel is also situated opposite each output light channel.

This arrangement can be used to measure the fluorescence of the medium flowing through the capillary tube.

In order to obtain accurate measurement results, the number of the individual fibers in each input light channel advantageously corresponds in each case to the number of the individual fibers in each assigned output light channel.

In a simple way, the optical conductors can be of flexible design, with the result that the light beams can be fed to the capillary tube without any problem.

This measure also renders it possible to reduce the overall size of the capillary tube holder according to the invention, since not only can the light beams be led over straight sections, as is known from the prior art, but in accordance with the possibilities for shaping the optical conductors virtually any shapes of the incoming and outgoing light leads are possible.

The optical conductors can comprise silica-silica fibers which, if appropriate, can be provided with a buffer coating, that is to say a suitable polymer coating, which increases the strength of the fibers used and protects the latter better against breakage.

In order for the capillary tube holder according to the invention to have access to as wide as possible a spectrum of application, it is possible to provide further optical conductors on the outside of the capillary tube holder, that is to say on the outside of the housing of the capillary tube holder, it being possible for the connecting elements to be constructed, for example, as pins or as standardized plug-in connections.

The capillary tube holder can thus be integrated in a simple way in already existing measuring arrangements in which optical conductors are used to feed light beams.

Some exemplary embodiments of the present invention are described in principle below with the aid of drawing, in which:

FIG. 1 shows a three-dimensional view of an inventive capillary tube holder in accordance with the arrow I of FIG. 2 [sic];

FIG. 2 shows a longitudinal section through the capillary tube holder according to FIG. 1 [sic];

FIG. 3 shows a diagram of a capillary tube holder according to the invention for measuring absorption;

FIG. 4 shows a diagram of a capillary tube holder according to the invention for measuring fluorescence;

FIG. 5 shows a diagram of a possible arrangement of individual fibers in a capillary tube holder according to the invention; and FIG. 6 shows a diagram of a section through a capillary tube holder according to the invention which is suitable for measuring fluorescence.

With reference to FIG. 1 [sic], a three-dimensional view of a capillary tube holder 1 is represented which has a recess 6, represented in FIG. 2, through which a capillary tube 2 of known design is guided. A medium which is represented in black in the capillary tube 2 for explanatory purposes flows through the capillary tube 2.

The recess 6 is arranged in a receptacle or a housing 3 of the capillary tube holder 1 and runs through the longitudinal axis thereof.

The capillary tube 2 is pushed into the housing 3 and fixed in the recess 6, and thus also in the housing 3, by means of a holding clamp 4.

The recess 6, which is arranged centrally in the housing 3 in the present exemplary embodiment, can be designed, for example, as a bore.

Arranged outside on the housing 3 of the capillary tube holder 1 are connecting elements which are constructed as pins 5, 5' and via which optical conductors, for example optical conductors constructed as single-note fibers (not represented), can be coupled in a suitable way to the capillary tube holder 1, it being possible to use the optical conductors (not represented) to lead light beams from a light source (not represented) to the capillary tube holder 1 via the pin 5, whereupon—as described at another juncture—the light beams are led through the capillary tube 2 and subsequently fed, via the pin 5', to an evaluation device such as, for example, a detector or a spectrometer.

Like other suitable connecting elements, as well, the pins 5, 5' can be fitted on the capillary tube holder 1 in any way known to the person skilled in the art.

FIG. 2 shows a longitudinal section through the capillary tube holder 1 of FIG. 1 [sic].

It can be seen from this view that provision is made in the axial direction of the recess 6, which runs through the entire housing 3 and is thus constructed as a through bore, of a pair of light channels which are arranged situated diametrically opposite one another with respect to the recess 6, the intention being for the light channel facing the pin 5 to be designated below as input light channel 7, and for the light channel facing the pin 5' to be designated below as output light channel 8.

The aim of the designations is to make clear that light beams fed from outside via the pin 5 are fed through the input light channel 7 to the capillary tube 2, which is arranged in the recess 6, as already mentioned, after which the light beams which have passed through the capillary tube and, of course, also through a medium flowing through the capillary tube 2, are fed to the pin 5' via the output light channel 8 and to the evaluation device via the optical conductors (not represented).

Arranged both in the input light channel 7 and in the output light channel 8 are cross section-transforming elements 9, 9' whose function is to be examined at a different juncture, it being the case that the cross section-transforming elements 9, 9' are arranged in each case at the end of optical conductors 10, 10' which faces the recess 6, and are thus a component of the optical conductors 10, 10'.

The optical conductor 10, which is arranged between the pin 5 and the cross section-transforming element 9 in the input light channel 7, is constructed as a fiber bundle and thus comprises individual fibers 11 (see FIG. 5), while by analogy with this an optical conductor 10' is provided in the output light channel 8 between the pin 5' and the cross section-transforming element 9'.

The optical conductors 10, 10' and the cross section-transforming elements 9, 9' are thus inserted into the respective light channels 7.

The optical conductors 10, 10' are of flexible design, with the result that the pins 5, 5' can be arranged at suitable points on the outside of the housing 3, and so the external dimensions of the capillary tube holder 1 represented can be substantially reduced. Again for this reason, it is no longer necessary, as required in the prior art, for the light channels 7, 8 to run in a straight line, rather they can also be arranged in curves, if appropriate.

The cylindrical capillary tube holder 1 represented has, for example, a longitudinal extent of about 30 mm and a diameter of approximately 15 to 20 mm.

In the exemplary embodiment represented, the cross section-transforming elements 9, 9' are arranged with a slight gap, which is represented enlarged in FIG. 2 for explanatory purposes, directly upstream of the capillary tube 2, with the result that up to approximately 90% of the light beams fed pass through the flowing medium, and this high proportion of useful light can subsequently be picked up by the downstream evaluation device and devaluated, with the result that the sensitivity of the detector device or evaluation device used is correspondingly high.

A capillary tube holder 1 having only one pair of light channels (input light channel 7, output light channel 8) is represented in FIGS. 1 and 2.

Of course, it is also within the discretion of the person skilled in the art to provide a capillary tube holder 1 having a plurality of pairs of light channels, as is represented diagramatically in FIGS. 3 and 4.

In this case, it is the aim below to use the same reference numerals for components already introduced in conjunction with FIGS. 1 and 2.

FIG. 3 shows a diagram of an arrangement of a capillary tube holder 1 which exhibits two pairs (not represented in more detail) of light channels with in each case one input light channel and one output light channel, an output light channel 8 and an input light channel 7 being situated in each case diametrically opposite one another with respect to the capillary tube 2, and the two pairs of light channels being arranged offset relative to one another by 90° with respect to the longitudinal axis 12 (see FIG. 5) of the capillary tube 2.

Such an arrangement is used to measure absorption in the medium flowing through the capillary tube 2.

In the case of this arrangement, as well, light beams are fed via the pin 5 to an optical conductor 10, the optical conductor 10 having a branch, however, with the result that in each case half of the light beams fed are led to each of the two cross section-transforming elements 9 represented. This split up of the incoming light beams is undertaken because the height and/or longitudinal extent of the capillary tube holder 1 is finite, and so only a certain number of individual fibers 11 (see FIG. 5) situated next to one another, for example, can open into the recess 6. Splitting up the light beams doubles the maximum possible number of individual fibers situated next to one another, and thus also improves the light yield.

After passing through the capillary tube 2, the light beams are picked up by the cross section-transforming elements 9' situated opposite in each case, and fed to the optical conductor 10', which has a branch in a fashion similar to the optical conductor 10, and relayed to the evaluation device (not represented) via the pin 5'.

The capillary tube holder 1 represented diagrammatically in FIG. 4 has a similar arrangement. By contrast with the arrangement according to FIG. 3, however, in the exemplary embodiment according to FIG. 4 the cross section-transforming elements 9 connected to the pin 5 are arranged in each case situated diametrically opposite one another with respect to the capillary tube 2. In a similar way, the cross section-transforming element 9' connected to the pin 5' are also arranged situated diametrically opposite one another in each case, it being possible to use this arrangement to measure the fluorescence in the medium flowing through the capillary tube 2, since two input light channels and two output light channels are situated opposite one another in each case.

Of course, it lies within the discretion of the average person skilled in the art also to provide even more light channels, for example four pairs, radially in the capillary tube holder 1 instead of the two pairs of light channels represented in FIGS. 3 and 4. Such an arrangement with a plurality of pairs of light channels which are arranged distributed radially in the recess 6 is represented greatly simplified for the purpose of measuring absorption in FIG. 6.

However, since evermore scattered light is produced as the number of light pairs increases, the possibility of measuring fluorescence can be impaired in the case of such an arrangement of a plurality of light channels, whereas measurements of absorption are not impaired.

FIG. 5 shows a diagram of a detail of a capillary tube holder, it being the case that in the cross section transforming elements 9, 9' represented, the individual fibers of the optical conductors 10, 10' (see FIG. 2) which are marked quite generally with the reference numeral 11, are split up such that they run parallel to the longitudinal axis 12 of the capillary tube 2, that is to say the originally round cross-sectional shape of the totality of the individual fibers 11 of the optical conductors 10, 10' is transformed into a straight line.

It is possible using this arrangement for a very large proportion of the light beams fed via the input light channel 7 to the cross section-transforming element 9 actually also to pass through the medium flowing through the capillary tube 2, and this represents a substantial advantage by contrast with the prior art, since in the case of known capillary tube holders a comparatively large proportion of the light beams fed is led through the outer wall of the capillary tube 2, resulting in a large decrease in the sensitivity of the evaluation device, and thereby an impairment of the measurement results.

Measurement results which are better by contrast with the prior art can be achieved in a simple way using the capillary tube holder described.

What is claimed is:

1. Capillary tube holder having a recess for holding a capillary tube, at least one pair of light channels being provided perpendicular to the axial direction of the recess, each pair of light channels having an input light channel for feeding light beams to the capillary tube and an output light channel for relaying the light beams to an evaluation device, and it being the case that the light channels run radially with respect to the recess and open into the recess, characterized in that optical conductors (9, 9' and 10, 10') composed of individual fibers (11) are provided in each input light channel (4) and each output light channel (8), the optical conductors (9, 9' and 10, 10') being arranged upstream of the capillary tube (2), and the diameter of each individual fiber (11) corresponding at least approximately to the inside diameter of the capillary tube (2), and a plurality of individual fibers (11) of the optical conductors (10, 10') being arranged parallel to and/or radially with respect to the longitudinal axis (12) of the capillary tube (2) in the region where the light channels (7, 8) open into the recess (6).

2. Capillary tube holder according to claim 1, characterized in that at their ends facing the recess (6), the optical conductors (10, 10') in each case have a cross section-transforming element (9, 9') for transforming the cross-sectional surface of the optical conductors (10, 10').

3. Capillary tube holder according to claim 1 or 2, characterized in that with respect to the recess (6) each output light channel (8) is situated diametrically opposite its assigned input light channel (7).

4. Capillary tube holder according to one of claims 1 to 3, characterized in that in the case of two pairs of light channels the two input light channels (7) and the two output light channels (8) are arranged in each case situated diametrically opposite one another with respect to the recess (6).

5. Capillary tube holder according to one of claims 1 to 4, characterized in that the number of the individual fibers (11) in each input light channel (7) corresponds in each case to the number of the individual fibers (11) in each assigned output light channel (8).

6. Capillary tube holder according to one of claims 1 to 5, characterized in that the optical conductors (10, 10') are flexible.

7. Capillary tube holder according to one of claims 1 to 6, characterized in that the optical conductors (10, 10') in each case have flat ends.

8. Capillary tube holder according to one of claims 1 to 7, characterized in that the optical conductors (10, 10') comprise silica-silica fibers.

9. Capillary tube holder according to claim 8, characterized in that the silica-silica fibers are provided with a buffer coating.

10. Capillary tube holder according to one of claims 1 to 9, characterized by connecting elements (5, 5') for further optical conductors on the outside of the capillary tube holder (1).

11. Capillary tube holder according to claim 10, characterized in that the connecting elements are constructed as standardized plug-in connections with pins (5, 5').

12. Capillary tube holder according to one of claims 1 to 11, characterized by fixing the capillary tube (2) in the recess (6) by means of a holding clamp (4).

* * * * *